United States Patent [19]
Cannon

[11] Patent Number: 5,403,274
[45] Date of Patent: Apr. 4, 1995

[54] PERFUSION CATHETER AND METHOD OF USE

[76] Inventor: Louis A. Cannon, 8344 Circlewood Dr., Saginaw, Mich. 48609

[21] Appl. No.: 31,584

[22] Filed: Mar. 15, 1993

[51] Int. Cl.⁶ .................. A61M 5/00; A61M 25/10; A61M 31/00; A61M 29/00
[52] U.S. Cl. ........................................ 604/9; 604/96; 604/101; 604/247; 604/53; 606/192
[58] Field of Search .................. 604/8–10, 604/96–103, 247, 49–54; 606/192–196; 600/18

[56] References Cited

U.S. PATENT DOCUMENTS

| | | |
|---|---|---|
| 4,661,094 | 4/1987 | Simpson . |
| 4,771,777 | 9/1988 | Horzewski et al. . |
| 4,790,315 | 12/1988 | Mueller, Jr. et al. . |
| 4,857,054 | 8/1989 | Helfer . |
| 4,877,031 | 10/1989 | Conway et al. . |
| 4,909,258 | 3/1990 | Kuntz et al. ............... 128/658 |
| 5,021,045 | 6/1991 | Buckberg et al. .......... 604/53 |
| 5,064,414 | 11/1991 | Revane ........................ 604/165 |
| 5,087,247 | 2/1992 | Horn et al. . |
| 5,129,887 | 7/1992 | Euteneuer et al. ......... 604/165 |
| 5,135,535 | 8/1992 | Kramer ....................... 606/194 |
| 5,137,513 | 8/1992 | McInnes et al. . |
| 5,158,540 | 10/1992 | Wijay et al. ................ 604/43 |
| 5,163,912 | 11/1992 | Gay et al. ................... 604/164 |
| 5,163,921 | 11/1992 | Feiring ....................... 604/247 |
| 5,180,364 | 1/1993 | Ginsburg .................... 604/53 |

FOREIGN PATENT DOCUMENTS 0464714 1/1992 European Pat. Off. ............ 604/102

Primary Examiner—John D. Yasko
Assistant Examiner—Adam J. Cermak
Attorney, Agent, or Firm—Brooks & Kushman

[57] ABSTRACT

An apparatus and method for passively perfusing blood past a stenosis during angioplasty. The apparatus utilizes a guide catheter having a plurality of openings in fluid communication with a guide lumen. A balloon catheter inserted within the guide catheter has a port located adjacent at least one of the openings in the guide catheter. A proximal balloon and a distal balloon may be utilized to respectively seal a distal end of the guide catheter and inflate the stenosis. A pressure equalization device, such as a syringe is utilized to initiate blood flow from an upstream blood vessel located proximal to the distal balloon to a downstream blood vessel located distal to the inflated distal balloon.

13 Claims, 4 Drawing Sheets

PERFUSION CATHETER AND METHOD OF USE

TECHNICAL FIELD

This invention relates to a perfusion catheter, and more particularly to a passive perfusion catheter for use in angioplasty.

BACKGROUND ART

Coronary angioplasty has gained wide acceptance as an alternative to open heart coronary bypass surgery for treatment of acute and chronic heart problems. A major contributory factor in such heart problems is a reduction in the nutrient blood flow to muscles of the heart which results from a reduction of blood flow through the coronary blood vessels. This reduction in flow may be caused by atherosclerotic plaque deposits on the walls of the affected blood vessels, which causes a narrowing of the lumen or channel of the blood vessel, referred to as a stenosis. This narrowing of the lumen has detrimental effects on the rate of blood flow therethrough which may cause the formation of a thrombosis or clot to occur.

The most common form of angioplasty is percutaneous translumenal coronary angioplasty (PTCA) which utilizes a catheter having an inflatable balloon at its distal end. These catheters are interchangeably referred to as dilatation, perfusion, angioplasty, PTCA or balloon catheters. The physician using fluoroscopy, guides the wire and/or the catheter through the vascular system until the balloon is positioned across the stenosis. The balloon is then inflated by supplying fluid under pressure through an inflation lumen to the balloon. The inflation of the balloon opens the blood vessel to re-establish acceptable blood flow through the blood vessel.

When the balloon is inflated during typical angioplasty procedures, all blood flow through the blood vessel is blocked. It is believed that long term inflation of the stenosis will increase the probability that the stenosis may remain open after dilation thereby reducing the risk of restenosis. Also, longer inflations often result in smoother molded luminal results, may decrease vessel trauma, and long inflations are currently used to repair injury caused by shorter inflation times during angioplasty procedures. However, typical dilation times range from about 30 to 60 seconds because longer inflation periods may result in dangerous ischemic conditions in areas distal to the inflated balloon in a blood vessel. This ischemic condition may be indicated by ST segment changes and dramatic increases in patient discomfort as well as a decrease in blood pressure. There is a belief that the restenosis rate can be lowered if longer inflation time is utilized for inflating the balloon while in a stenosis to reduce patient discomfort so that the stenosis will remain open and not restenose. To accomplish longer inflation times, there is a need to provide sufficient blood flow to the portions of the heart distal of the stenosis during inflation.

Several approaches have been adopted in an attempt to address the problem of maintaining blood flow and hence preventing ischemia and ST segment changes during prolonged dilatations. Initial attempts to overcome this problem relied on passive perfusion catheters. Passive perfusion catheters which have been proposed in the past have utilized at least one opening in the guide catheter and/or the dilatation catheter both immediately proximal and distal to the inflated balloon. However, initial attempts at passive perfusion often resulted in sub-optimal blood flow through the dilatation catheter. Several attempts have been made to overcome this sub-optimal blood flow. Examples of such attempts may be seen in U.S. Pat. Nos. 4,661,094 to Simpson, 4,877,031 to Conway et al., 5,087,247 to Horn et al., and 4,790,315 to Mueller, Jr., et al.

In each of the above-referenced patents, attempts were made to vary either the size or shape of the openings, vary their spacing and location relative to each other and about the guide catheter and/or dilatation catheter. Varying the size, shape, location and spacing of the openings has done little to overcome the problem of sub-optimal flow associated with passive perfusion.

Active perfusion has been attempted to overcome the problem of maintaining sufficient blood flow during extended periods of dilatation which known attempts at passive perfusion have been unable to solve. Active perfusion utilizes a mechanical pump to force blood and/or other fluid through the balloon catheter.

Original attempts at active perfusion required withdrawing the blood from apertures at an upstream location and delivering the blood to the pump itself and to processing stations located ex vivo, and then returning it to the catheter to be expelled back into the blood vessels and apertures located downstream of the intake apertures. Examples of such an approach may be found in U.S. Pat. No. 5,137,513 to McInnes et al., and U.S. Pat. No. 5,158,540 to Wijay et al. An alternative approach was to provide a perfusion catheter and pump arrangement wherein the blood or other body fluid was drawn into the catheter, bypassing the obstruction, and then immediately expelling the blood under pressure, without undergoing an ex vivo loop. An example of this approach may be seen in U.S. Pat. No. 4,857,054 to Helfer.

Regardless of the approach, all forms of active perfusion require some form of mechanical pump which necessitates additional equipment thereby complicating the angioplasty procedure. In addition, pumping blood up to high pressures has a potential effect of causing hemolysis.

The present invention incorporates many of the known benefits of both active and passive perfusion while improving the passive perfusion catheters.

DISCLOSURE OF INVENTION

An apparatus and method is provided for passively perfusing blood past a stenosis during angioplasty. A guide catheter is provided which has a proximal end, a distal end and a guide lumen which extends therethrough. The guide catheter defines at least one opening toward the distal end of the guide catheter. A balloon catheter is also provided which is located within the guide lumen. The balloon catheter has a proximal end, a distal end and defines a first balloon lumen which extends therethrough. The balloon catheter has an aperture located toward its distal end. A distal balloon is located toward the distal end of the balloon catheter and a proximal balloon is located proximal to the distal balloon and the distal end of the guide catheter. The proximal balloon is also located distal to the guide catheter opening and the balloon catheter aperture. A pressure equalization means is provided which is in fluid communication with the guide catheter for equalizing the pressure between the upstream blood vessel (aorta) and an area proximal to the distal balloon when the proximal balloon and the distal balloon are inflated. The pressure equalization means is utilized to initiate passive perfusion of blood from the upstream blood vessel into the opening of the guide catheter, then through the aperture of the balloon catheter and out the distal end of the balloon catheter into the downstream blood vessel. Once the blood flow is initiated by the pressure equalization means, it is passively maintained by the existing pressure gradient within the human body.

Accordingly, a specific object of the present invention is to provide an improved perfusion catheter having increased volume of blood flow during inflation of the balloon without requiring the use of a pump.

Another object of the present invention is to provide an inexpensive catheter utilizing a passive perfusion catheter having increased blood flow capabilities during inflation of the balloon.

An additional object of the present invention is to provide an easy to use and effective catheter utilizing passive perfusion capable of increasing the dilatation time in excess of presently established limits.

An advantage of the present invention is the improved blood flow during balloon inflation thereby greatly increasing the length of dilatation.

A further advantage of the present invention is to have increased dilatation periods and controlled pressure due to increased blood flow.

A feature of the present invention is to obtain increased blood flow without the use of a mechanical pump.

A further feature of the present invention is to equalize hemostatic pressure between the blood vessel and the perfusion catheter in order to optimize the pressure gradient between the upstream and downstream blood in order that passive perfusion is maximized.

The above objects, features and advantages of the present invention are readily apparent from the following detailed description of the invention when taken in connection with the accompanying drawings.

BEST MODE(S) FOR CARRYING OUT THE INVENTION

The embodiment illustrated in FIGS. 1-7 shows a passive perfusion apparatus that relies on priming the pressure gradient between the aorta (upstream blood vessel) and the distal coronary artery (downstream blood vessel) to initiate the flow gradient for passive blood flow, generally indicated at 10, which is intended for use in percutaneous translumenal coronary angioplasty (PTCA) to dilate a stenosis AA in an attempt to prevent restenosis. In this procedure, a guide (not shown) is inserted into the femoral artery of a patient and fed toward a blood vessel BB having the stenosis. Once it is located in the desired position, a guide catheter 12, is inserted into the blood vessel over the guide.

Figure 4:
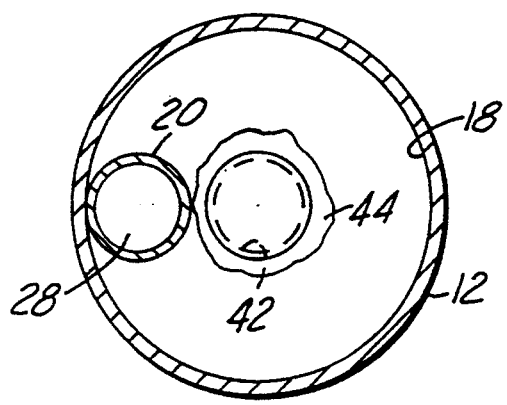
FIG. 4 is a cross-sectional view taken along line 4—4 of FIG. 1 showing the central lumen of the balloon catheter with both balloons deflated.
Figure 5:
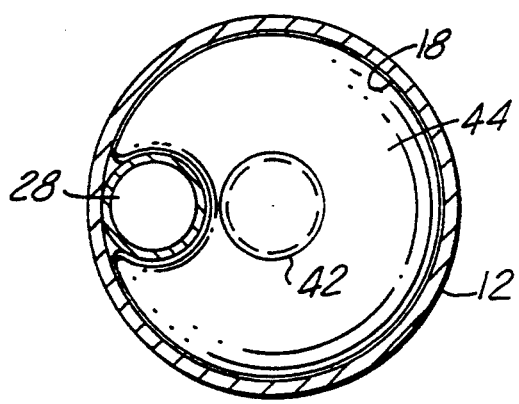
FIG. 5 is a cross-section taken along line 5—5 of FIG. 2 with the trapper balloon inflated.

In this embodiment, the guide catheter 12 has a distal end 14 which is farthest from the physician when located within the blood vessel and a proximal end 16 which protrudes outside the patient. The guide catheter 12 has an internal passageway or channel 18 which extends from the proximal end 16 to the distal end 14. In this embodiment, the channel (a/k/a "guide lumen") 18 has a generally circular cross section as shown in FIGS. 4 and 5 with an outside diameter ranging between 7 F (0.072 mm > X > 0.068 mm) and 11 F (0.086 mm < - X < 0.109 mm) inside diameter which is slightly smaller.

Once the guide catheter 12 is located in the desired position, the guide (not shown) is removed from the patient. A balloon catheter 20 is then inserted within the guide lumen 18 of the guide catheter 12. The balloon catheter 20 has a distal balloon 22 which is circumferentially mounted about a distal end 24 of the balloon catheter 20. A guide wire 38 typically is placed distal to the area of blockage and the balloon catheter 20. Conventional guide wires have an external diameter ranging between 0.010 mm to 0.018 mm. The balloon catheter 20 is inserted past the distal end 14 of the guide catheter 12 and into the blood vessel BB over the guide wire previously placed until a marker 26 located within the distal balloon 22 indicates that distal balloon 22 is centrally located on the stenosis AA (see FIGS. 2 and 3). Typical distal balloon lengths range between 10 mm–40 mm and have a diameter ranging between 1.5 to 6.0 mm.

Figure 7:
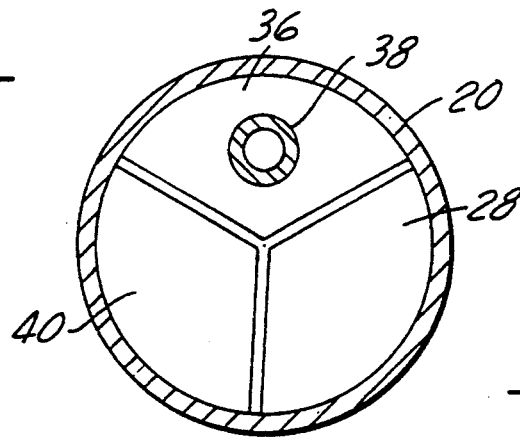
FIG. 7 is a cross-section taken along line 7—7 of FIG. 3 showing the first, second and third balloon lumens of the balloon catheter.

As shown in FIG. 7, the balloon catheter 20 has an external diameter which ranges from 1.8 F to 3.3 F. The balloon catheter defines a first lumen 28, shown in FIGS. 3 and 7, which extends from a proximal end 30 to the distal end 24. The balloon catheter 20 also defines an aperture or port 32 which enables the lumen 28 to be in fluid communication with the guide lumen 18. A hole 34 is located at the distal end of the balloon catheter to enable discharge of fluids. In this embodiment, the balloon catheter 20 also defines a second lumen 36 for slidably receiving the guide wire 38 which assists in feeding the balloon catheter to the stenosis. A third lumen 40 is defined within the balloon catheter and extends from the proximal end 30 to the distal balloon 22 for selective inflation and deflation (venting) of the distal balloon 22.

A trapper 42 is then inserted into the guide catheter 12 in parallel alignment with the balloon catheter 20. A balloon 44 is located on a distal end 46 of the trapper 42. The trapper 42 is located within the guide lumen such that the trapper balloon 44 is located within the distal end of the guide catheter 12, proximal to the distal balloon 22 and distal to the port 32 and at least one opening 48 located on the guide catheter 12. The guide catheter 12 may have more than one opening 48 to enable fluid communication between the blood vessel BB and the guide lumen 18. In an alternative embodiment, the guide catheter may have a one way valve 49 located on at least one opening 48 to prevent fluid from escaping externally from the guide lumen 18 into the blood vessel BB, while allowing the fluid from the blood vessel to enter the guide lumen 18.

An adapter 50 is sealably removably connected to the proximal end 16 of the guide catheter 12. The adapter 50, of this embodiment, has a central lumen 52 and a side arm 54 in fluid communication with the central lumen 52. The central lumen 52 and the side arm 54 each have a Luer fitting (ring) 55 which selectively seals or provides access to the central lumen 50, which is in fluid communication with the guide lumen 18. When open, the balloon catheter 20 and the trapper 42 may be inserted into the guide catheter 12. When closed, the central lumen 52, and side arm 54 are water tight.

A manifold 56 is attached to the side arm 54 of the adapter 50. The manifold 56 has three valves 58a–c which are respectively attached to a pressure monitor (PM), a saline solution (SS), and a contrast solution (CS). A syringe (pressure equalization means) 60 is attached to an opposite end of the manifold 56. A container capable of drawing fluid from the guide catheter 12 and blood vessel BB to equalize the pressure and exert force to initiate passive blood flow may be substituted for the syringe 60. The syringe 60 is used to selectively draw fluid from one of the solutions by pulling back or drawing out a plunger 62 of the syringe in combination with the valves 58a–c. Then pushing the fluid into the guide lumen 18 by pushing the plunger 62 back into the syringe 60.

Once all the elements are in place, the distal balloon 22 and the proximal balloon 44 are inflated by the introduction of saline into the third balloon lumen 40 and the trapper 42, respectively. The saline is introduced by a second syringe 64 attached to the proximal end of the trapper 42 and a third syringe or other supply means (not shown) attached to the proximal end 30 of the balloon catheter 20.

Figure 1:
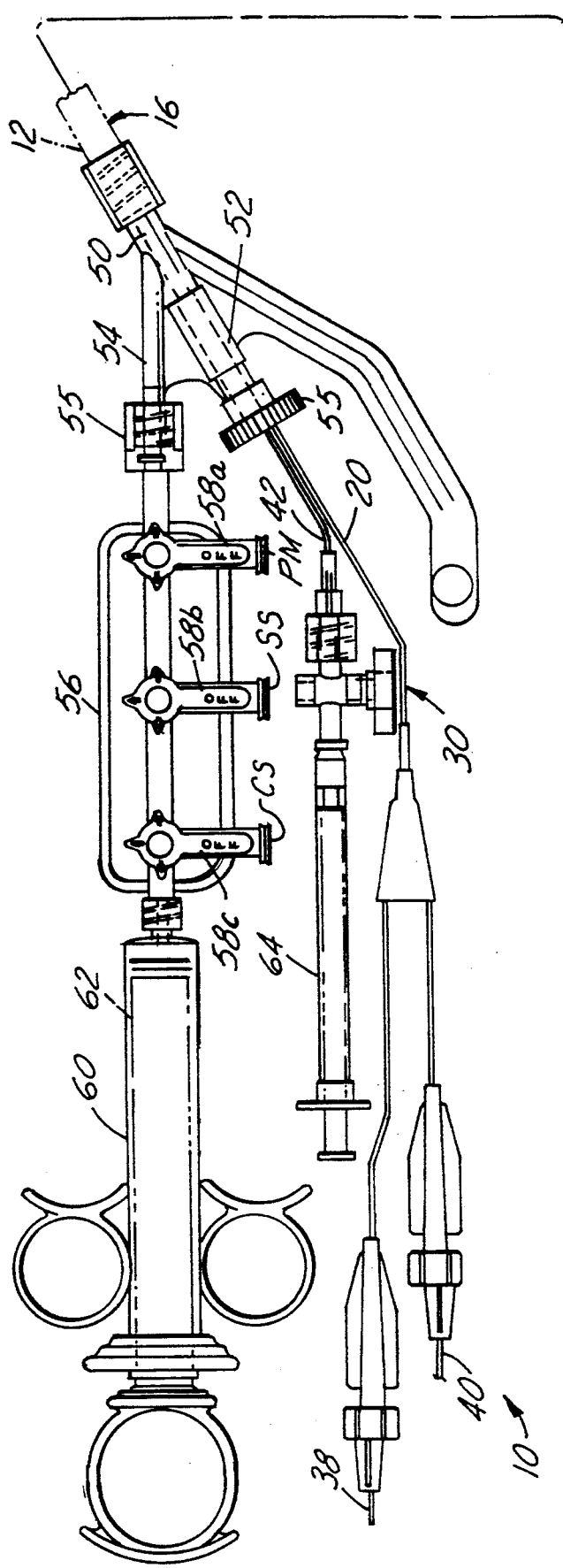
FIG. 1 is a side view of a catheter, partially broken away, showing a portion of the internal elements of the present invention.
Figure 1:
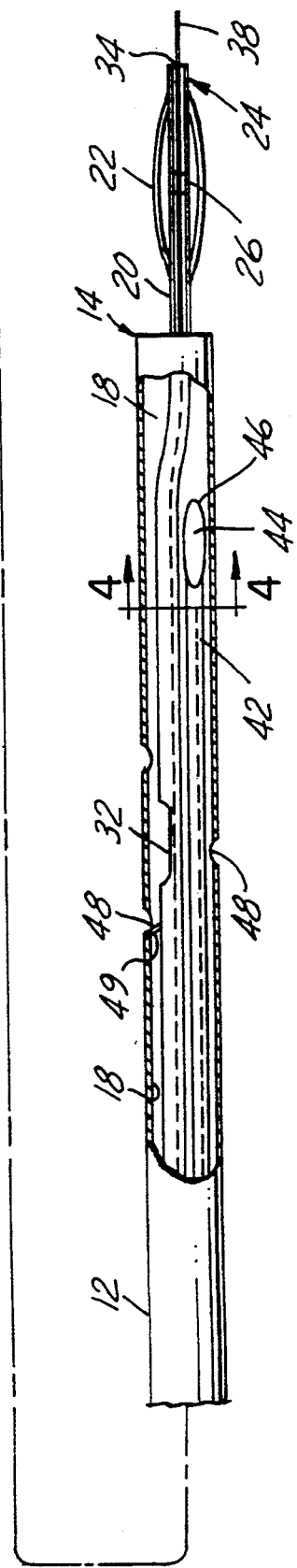
Figures 2, 3:
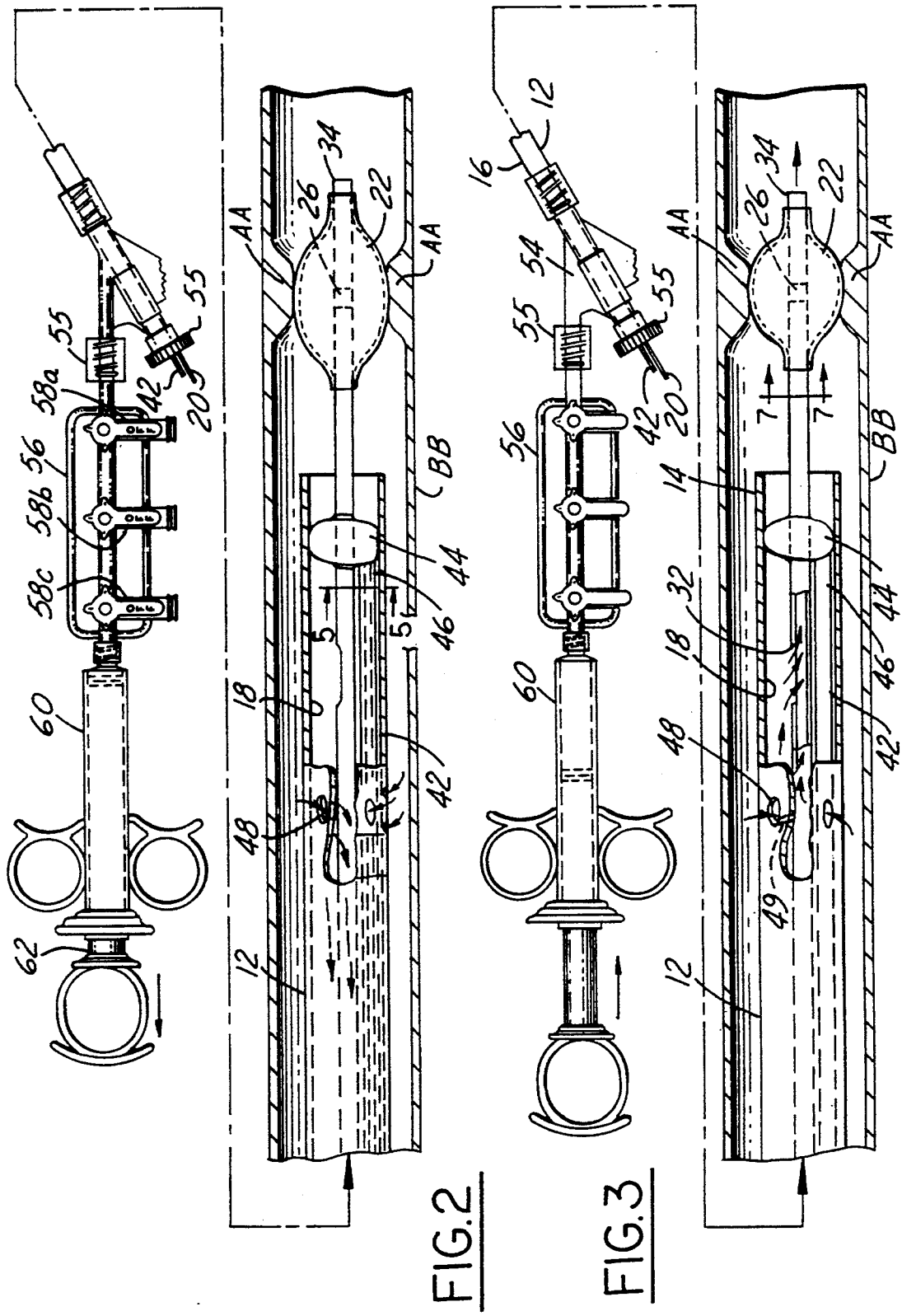
FIG. 2 is a side view similar to that shown in FIG. 1, partially broken away, showing both balloons inflated and with the plunger drawing blood toward the proximal end of the catheter.
FIG. 3 is a similar view to that shown in FIGS. 1 and 2 showing the plunger priming the system by moving toward the distal end and showing the blood flowing from upstream to downstream in accordance with the present invention.

As shown in FIGS. 2 and 3, inflation of the distal balloon 22 results in dilation of the stenosis which has the negative effect of preventing passive flow of blood or other fluids around the distal balloon 22. The inflation of the trapper balloon 44 effectively seals the distal end of the guide catheter 12, as may be seen in FIGS. 2, 3, and 5. In order to initiate passive perfusion of blood, a physician draws back the plunger 62 (a predetermined distance) to draw fluid (a predetermined amount) from the blood vessel BB into the syringe 60, thereby filling an area proximal to the distal balloon 22, including the guide catheter 12, the guide lumen 18, the balloon first lumen 28, the adaptor 50, the manifold 56, the syringe 60 and the blood vessel AA with fluid.

The filling of this area equalizes the pressure between the blood vessel, the guide catheter 12, the guide lumen 18, and the first balloon lumen 28. The physician applies pressure (a predetermined amount) to the plunger 62 to force fluid into the guide lumen 18 to initiate flow from the blood vessel, into the opening 48, into the port 32, through the first balloon lumen, past the inflated balloon 44 and the inflated distal balloon 22, and out the opening 34 at the distal end 24 of the balloon catheter 20. The result is that the fluid then takes advantage of the natural pressure gradient to passively flow from the higher pressure (approximately 120 mmHg) in the upstream blood vessel (proximal to the distal balloon 22) to the downstream blood vessel (distal to the distal balloon 22) which has relatively lower pressure (approximately 6–12 mmHg), thus providing the downstream blood vessel with sufficient oxygenated blood flow to prevent ischemic conditions. The result is that the inflation of the distal balloon 22 may be significantly prolonged which results in an improved angioplasty procedure.

An alternative embodiment of the present invention, is to have both the proximal and distal balloons 44 and 22, respectively located on the balloon catheter and be capable of simultaneous inflation and deflation through the first balloon lumen.

A further embodiment of the present invention is to mount the balloon 44 within the guide lumen 18 of the guide catheter 12 rather than utilizing a two balloon catheter or a separate trapper.

Figure 6A:
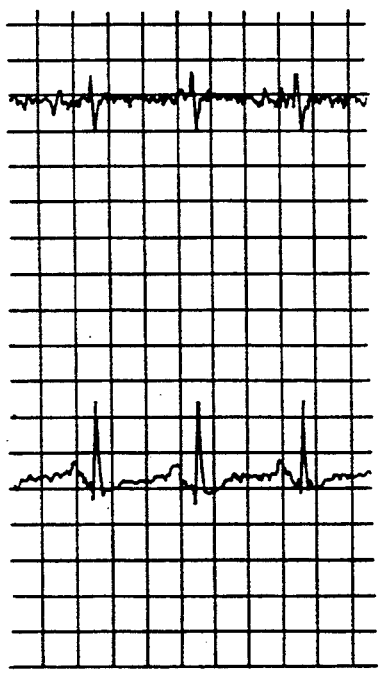
FIG. 6A is a printout from an EKG heart monitor showing the QRST curve as well as a pressure reading the heart in its normal position without the balloons inflated.

FIGS. 6A through 6D illustrate the advantages of the present invention in actual use under normal angioplasty conditions. FIG. 6A illustrates a normal EKG reading and a virtually flat pressure reading prior to the angioplasty procedure.

Figure 6B:
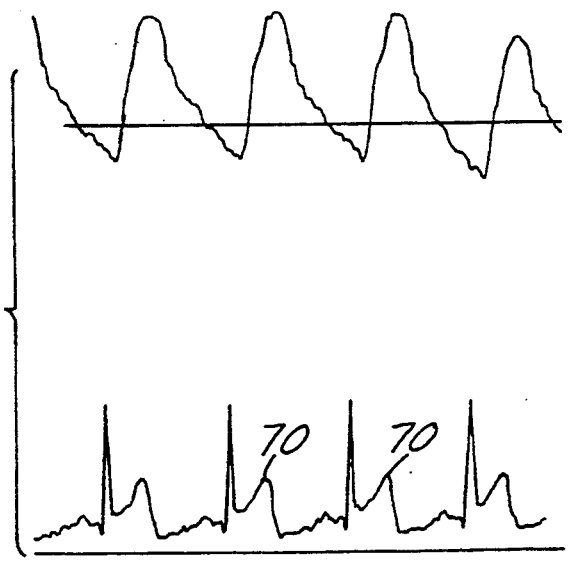
FIG. 6B depicts a significant ST segment change when the distal balloon is inflated during installation relying exclusively on standard passive perfusion through use of holes in the guide catheter and a port in the balloon catheter.

FIG. 6B illustrates reliance on passive perfusion using standard teachings where holes 48 have been made in the guide catheter 12 and the guide wire has been removed. No use has been made of the present invention. The pressure readout reflects inflation of the distal balloon 22 in accordance with accepted angioplasty procedures. Note the significant ST segment change 70 after approximately 2 minutes of distal balloon inflation. At this point, a patient typically complains of severe chest pain.

Figures 6C, 6D:
FIG. 6C depicts the EKG readout as well as the pressure readout when both balloons are inflated and the guide wire removed in accordance with the present invention.
FIG. 6D depicts the change in the amplitude of the ST segment when the guide wire is reinserted into the guide catheter partially obstructing perfusion.

FIG. 6C illustrates the results with use of the present invention and after more than six minutes of distal balloon inflation. Note that there is only minimal or virtually no ST segment change and the patient is not likely to experience any chest pain. The pressure readout reflects inflation of both the distal balloon and the trapper balloon in accordance with the present invention.

FIG. 6D again shows the use of the present invention and illustrates the results when the guide wire 38 is reinserted into the balloon catheter distal to the port 32, thereby obstructing or reducing the passive flow of blood. Note that in FIGS. 6B and 6C, the guide wire 38 was removed or withdrawn proximal to the port.

While the best mode for carrying out the invention has been described in detail, those familiar with the art to which this invention relates will recognize various alternative designs and embodiments for practicing the invention as defined by the following claims.

What is claimed is:

1. An apparatus for passively perfusing blood past a stenosis in a blood vessel during angioplasty, the apparatus comprising:

a guide catheter having a proximal end, a distal end, and defining a guide lumen extending therethrough, the guide catheter having at least one opening adjacent the distal end of the guide catheter;

a one-way valve means for allowing blood to flow into said guide lumen and preventing blood from flowing from said guide catheter into said blood vessel;

a balloon catheter located within the guide lumen, the balloon catheter having a proximal end, a distal end, and defining a first balloon lumen extending therethrough, the balloon catheter having an aperture located adjacent the distal end of the balloon catheter;

a first balloon located toward the distal end of the balloon catheter;

a second balloon located proximal to said first balloon and said distal end of the guide catheter, the second balloon located distal to said guide catheter opening and said balloon catheter aperture;

means in fluid communication with the guide catheter for maintaining fluid flow between the upstream blood vessel and an area proximal to said first balloon, when said second balloon and said first balloon are inflated, to allow passive perfusion of blood from the upstream blood vessel into said at least one opening of the guide catheter, through said aperture of the balloon catheter, and out the distal end of said balloon catheter into the downstream blood vessel;

said second balloon being located on a trapper and slidably inserted within said guide catheter.

2. The apparatus of claim 1 wherein said first balloon is mounted at the distal end of said balloon catheter.

3. The apparatus of claim 1 wherein said second balloon is mounted proximal to said first balloon and distal to said aperture in said balloon catheter.

4. The apparatus of claim 1 further including a second balloon lumen extending from the proximal end of said balloon catheter to said first balloon for selective simultaneous inflation and deflation of said second balloon and said first balloon.

5. The apparatus of claim 1 further comprising an adapter having a central lumen and at least one side member in fluid communication with said central lumen for inserting said balloon catheter into said guide catheter.

6. The apparatus of claim 1 wherein said first balloon and said distal end of said balloon catheter extend beyond said distal end of the guide catheter.

7. The apparatus of claim 1 wherein said first balloon lumen is adapted to slidably receive a guidewire.

8. The apparatus of claim 1 wherein said at least one opening in the guide catheter and said aperture in the balloon catheter are in fluid communication.

9. A method of passively perfusing blood during angioplasty, comprising:

inserting a guide catheter having a guide lumen extending therethrough into a blood vessel of a patient;

inserting a balloon catheter through the guiding catheter;

inflating a distal balloon on the balloon catheter to dilate a stenosis;

inflating a proximal balloon to create a seal between the guide catheter and the balloon catheter;

drawing a sufficient predetermined volume of fluid from the blood vessel of the patient through the guide lumen in the guide catheter to partially fill a container outside the guide catheter and to fill the guide catheter and the balloon catheter with fluid from the blood vessel and equalizing pressure therebetween; and applying a predetermined pressure on the predetermined volume to return the fluid to the guide lumen, the guide catheter and the blood vessel thereby filling the guide catheter and the blood vessel to initiate blood passive flow from the blood vessel through the guide catheter and the balloon catheter to bypass the distal balloon to insure passive perfusion of blood when the distal balloon and proximal balloon are inflated.

10. A method of passively perfusing blood past a stenosis in a blood vessel during angioplasty, the steps comprising:

inserting a guide catheter within said blood vessel, the guide catheter having a distal end and an opening adjacent said distal end;

positioning a balloon catheter through said guide catheter to centrally locate a first balloon on said stenosis;

inflating said first balloon to dilate said stenosis, thereby preventing blood flow around said first balloon;

inflating a second balloon to seal said distal end of said guide catheter;

drawing fluid from said blood vessel and said guide catheter into a syringe means and also filling the guide catheter and the balloon catheter with fluid and equalizing the pressure therebetween; and depressing said syringe means to initiate passive blood flow from said blood vessel to said guide catheter, through said balloon catheter and past said inflated first balloon into said blood vessel distal to the inflated first balloon.

11. A method of passively perfusing blood during angioplasty, comprising:

inserting a guide catheter having a guide lumen extending therethrough into a blood vessel of a patient;

inserting a balloon catheter through said guide catheter;

inflating a first balloon on said balloon catheter to dilate a stenosis;

drawing a sufficient predetermined volume of fluid from the blood vessel of the patient through the guide catheter to partially fill a container outside the guide catheter and to fill at least portions of the guide catheter and the balloon catheter with fluid from the blood vessel; and applying a predetermined pressure on the predetermined volume to return said fluid through said balloon catheter, guide catheter and blood vessel thereby filling the guide catheter and the blood vessel to initiate blood passive flow from the blood vessel through the guide catheter and the balloon catheter to bypass the first balloon to insure passive perfusion of blood when the first balloon is inflated.

12. The method as set forth in claim 11 further comprising the step of inflating a second balloon to create a seal between said guide catheter and said balloon catheter.

13. The method as set forth in claim 11 further comprising the step of providing a one-way valve on said guide catheter.

* * * * *